United States Patent [19]

Davison

[11] Patent Number: 4,710,075

[45] Date of Patent: Dec. 1, 1987

[54] ADJUSTABLE DRILL GAUGE

[75] Inventor: Dale Davison, Warsaw, Ind.

[73] Assignee: Boehringer Mannheim Corporation, Indianapolis, Ind.

[21] Appl. No.: 914,079

[22] Filed: Oct. 1, 1986

[51] Int. Cl.[4] .............................................. B23B 51/00
[52] U.S. Cl. .................................. 408/202; 33/169 B; 33/173; 408/226; 408/241 S
[58] Field of Search ..................... 408/202, 226, 241 S, 408/72 B, 115 B; 409/214, 218, 220; 33/169 B, 173, 201, 567

[56] References Cited

U.S. PATENT DOCUMENTS

| 2,833,168 | 5/1958 | Nelson | 408/202 |
| 4,039,266 | 8/1977 | O'Connell | 408/202 |
| 4,341,206 | 7/1982 | Perrett et al. | 128/92 B |
| 4,354,779 | 10/1982 | Vaughan | 408/202 X |

Primary Examiner—Z. R. Bilinsky
Assistant Examiner—Glenn L. Webb

Attorney, Agent, or Firm—Barnes & Thornburg

[57] ABSTRACT

A drill stop apparatus for use with an elongated drill bit is provided. The drill bit has a drilling end that is used to drill a hole of a specified, predetermined depth. The bit also has a plurality of circumferentially extending, axially spaced grooves formed on its outer surface. The drill stop includes a body having a first end and formed to include an axially extending bore that is sized to receive the drill bit to permit the bit to be moved axially within the body. The body also has a cavity that extends substantially perpendicularly through the bore. A plunger is provided that is sized to be received in the cavity for releasably engaging one of the plurality of grooves in the drill bit to lock the drill bit against axial movement within the body member such that a specified length of the drill bit extends beyond the first end of the body member. This specified length of the drill bit defines a specified operable drilling length between the first end of the stop apparatus and the drilling end of the drill bit.

10 Claims, 5 Drawing Figures

U.S. Patent Dec. 1, 1987 Sheet 1 of 2 4,710,075
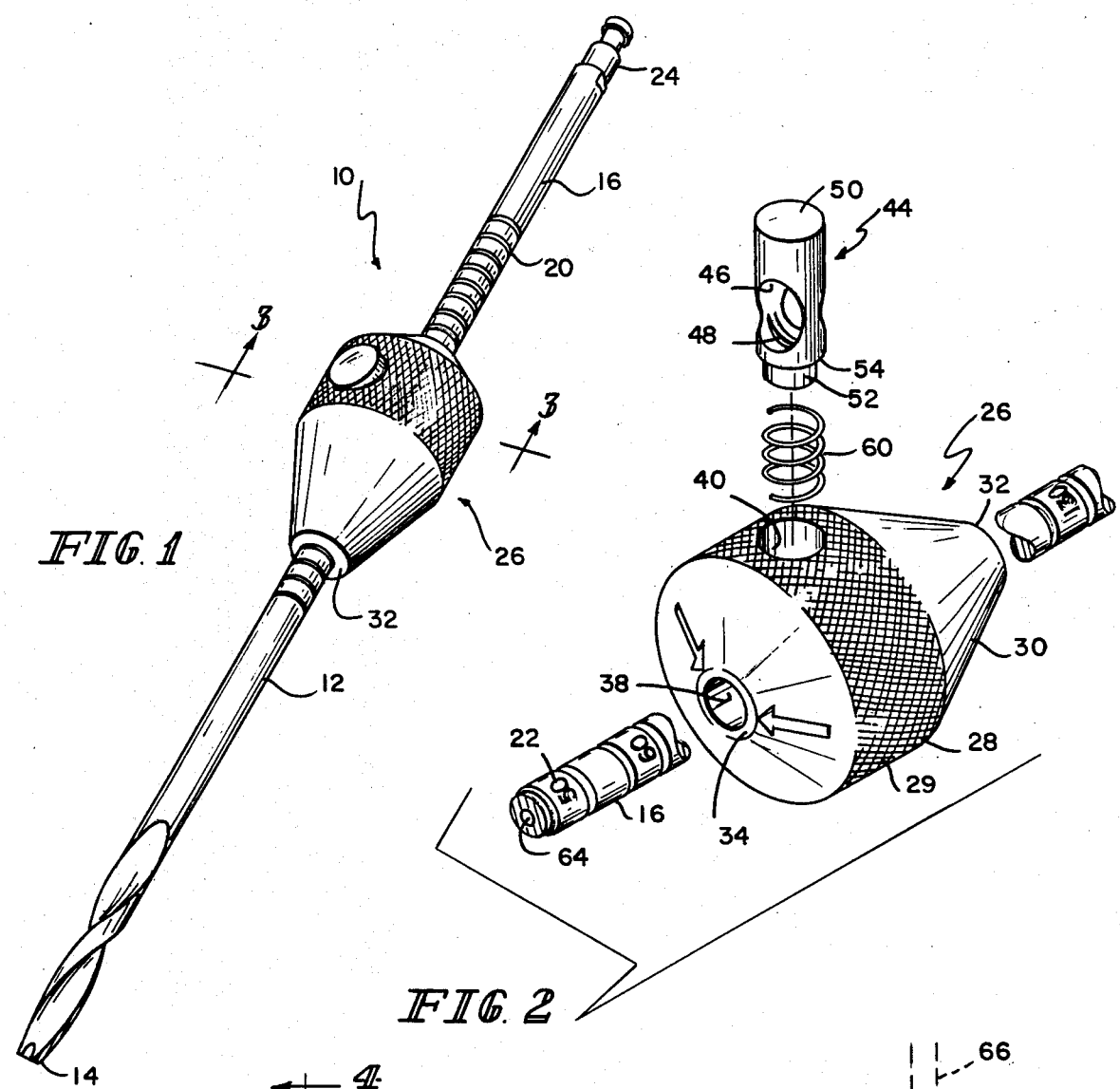
FIG. 1
FIG. 2
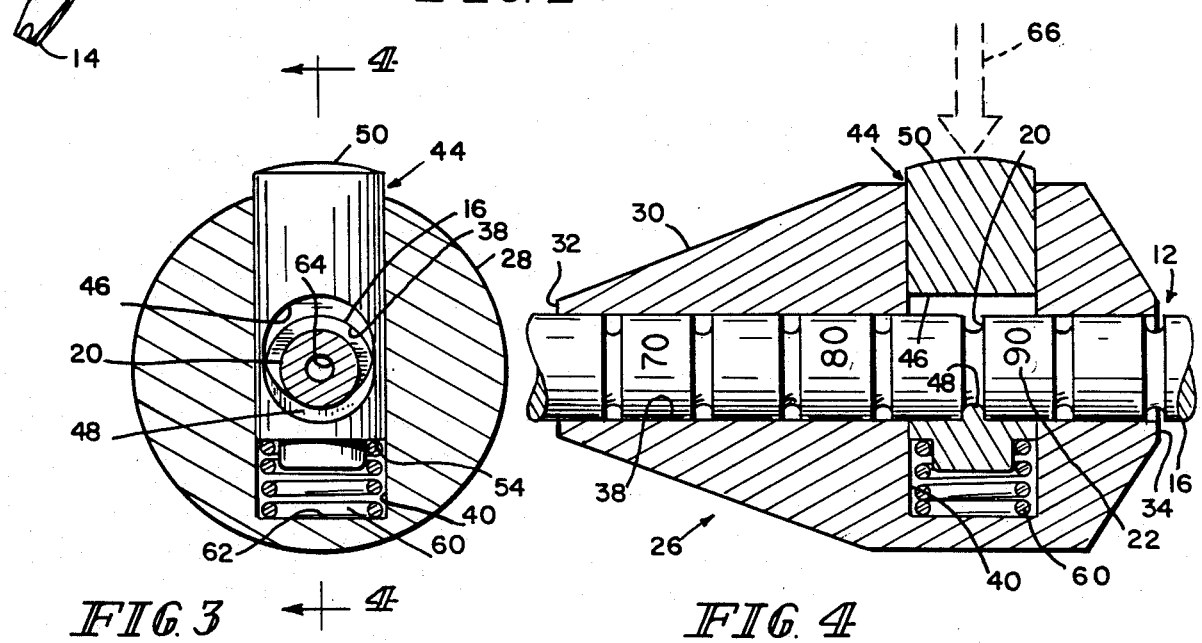
FIG. 3
FIG. 4

ADJUSTABLE DRILL GAUGE

BACKGROUND AND SUMMARY OF THE INVENTION

The present invention relates to a drill for boring a hole of a specified depth in bone. More particularly, the present invention relates to an adjustable stop member mounted on the drill that is selectively movable to different positions along the drill shaft to provide a positive stop to control the depth of penetration of the drill bit. The adjustable stop member of the present invention can be used to control the depth of any drilling operation in bone, including depth drilling for tibial tray screw fixation and drilling for femoral screw implant.

One example of the use of a bone drill is in the surgical treatment of fractures of the neck of the femur. Such treatment generally requires reduction of the fracture by means of a screw implant. The implant is designed to bring the fractured surfaces together, and to stabilize the fractured surfaces in proper alignment for healing. Before such a screw implant can be inserted into the bone, a hole must be drilled into the bone. Generally, the hole has a diameter somewhat smaller than the diameter of the screw implant. The screw implant is generally provided with self-tapping threads which screw into the smaller diameter hole to firmly embed the implant in the bone. In order for the screw implant to be anchored properly in the bone, it is desirable to drill the hole as deeply as possible through the neck and into the head of the femur, but not to pass entirely through the opposite surface of the head of the femur.

To drill the hole into the neck and head of the femur, a drill assembly is normally used that includes some type of stop collar to limit the penetration of the drill bit into the bone. Normally, drilling of the hole is preceded by the placement of a conventional guidewire, for example a ⅛ inch guide pin. The guide pin is generally placed in the bone by the use of an alignment device that assures that the pin will be placed at the proper angle. The guide pin is normally placed in the bone to extend from the outer, or lateral portion of the femur through the fracture, and into the head of the femur to a point near the surface of the head. The guide pin is generally inserted using x-ray information to determine when the pin has reached the desired position and depth. After the pin has been inserted to the proper depth, the protruding remainder of the pin is measured with a measuring device that permits the surgeon to determine the length of the hole to be drilled into the bone. Once this length, or depth of the hole, is determined, the drill assembly is adjusted so that a hole of the proper depth can be drilled. Generally, the drill assembly will have a cannulated drill bit to permit the drill bit to be inserted directly over the guide pin so that the hole can be drilled with the wire in place. Drilling the hole over the guide pin insures that the hole will be drilled at the proper angle, and at the proper position in the bone.

One type of tool for drilling a hole of a specified depth in a bone is disclosed in U.S. Pat. No. 4,341,206 to Perrett et al. U.S. Pat. No. 4,341,206 discloses a tool that includes a drill to form a small diameter hole with a reamer portion to form a slightly larger diameter hole disposed over the drill. The drill and the reamer portion are axially adjustable relative to each other, with the reamer portion acting as a stop collar for the drill. The shank of the drill has a number of annular grooves with calibration marks. A locking device is attached to the reamer portion to lock the reamer portion against movement with respect to the drill. The locking device is in the form of a sleeve that extends axially away from the reamer portion. The sleeve has a plurality of cuts that are parallel to the longitudinal axis of the drill to form four tongues that extend in the longitudinal direction of the drill and resiliently engage the grooves of the shank of the drill. A threaded nut is provided that engages the tongues to lock the tongues in a preselected groove to determine the amount of extension of the drill bit beyond the end of the reamer portion.

One problem with the device disclosed in U.S. Pat. No. 4,341,206 is that the adjustable locking device on the reamer portion is difficult to adjust axially along the shank of the drill. To adjust the drill with respect to the reamer, or stop collar, the threaded nut must be first disengaged from the tongues. After the nut is disengaged, the operator must grasp the reamer portion with one hand, and the shank of the drill with the other hand, and move the shank of the drill within the reamer portion. A substantial amount of force is required to move the two components relative to each other because of the resilient locking characteristics of the tongues in the groove.

Another problem with the tool disclosed in U.S. Pat. No. 4,341,206, is that the threaded nut is removed from the locking device by rotation. Because of this rotational activation of the threaded nut, it is possible for the nut to become disengaged from the locking device during operation of the drill. This can possibly result in movement of the reamer portion along the shank of the drill during the drilling procedure, which can possibly lengthen the amount of the drill extending beyond the reamer portion. This may cause the drill to protrude through the surface of the neck of the femur.

One object of the present invention is to provide a drill assembly that includes a stop member that is easily adjustable along the shank, or shaft of the drill. Preferably, the stop member will be adjustable by the use of one hand only.

Another object of the present invention is to provide a drill assembly in which the locking capability of the stop member is not affected by rotation of the drill bit.

According to the present invention, a drill stop apparatus for use within an elongated drill bit having a drilling end used to drill a hole of a specified, predetermined depth, is provided. The drill bit has a plurality of circumferentially extending, axially spaced grooves formed on its outer surface. The stop apparatus includes a body having a first end and formed to include an axially extending bore that is sized to receive the drill bit to permit the drill bit to be moved axially within the body. The body also has a cavity that extends substantially perpendicularly through the bore. Means are disposed in the cavity for releasably engaging one of the plurality of grooves in the drill bit to lock the drill bit against axial movement within the body member such that a specified length of the drill bit extends beyond the first end of the body member. This specified length of the drill bit defines a specified operable drilling length between the first end of the stop apparatus and the drilling end of the drill bit.

One feature of the foregoing structure is that the body member is formed to include a cavity that extends substantially perpendicular to the drill bit receiving bore. Means are disposed in the cavity for releasably engaging one of the plurality of grooves in the drill bit to lock the drill bit against axial movement within the body member. One advantage of this feature is that the engaging means operates along an axis substantially perpendicular to the axis of the drill bit. Thus, the engaging means, or locking mechanism for the body member, can be completely disengaged simply by moving the engaging means along this substantially perpendicular axis.

In preferred embodiments of the present invention, the engaging means comprises a plunger that is sized to be movably received within the body member cavity. The plunger is formed to include a transverse opening that is sized to receive the drill bit and an upstanding ridge that is configured to engage selectively one of the grooves in the drill bit. One feature of the foregoing structure is that the groove-engaging ridge is connected to the movable plunger. One advantage of this feature is that by simply moving the plunger, the ridge may be disengaged from the groove to permit the body member to move with respect to the drill bit to adjust the operable length of the bit.

Also in preferred embodiments of the present invention, spring means are provided for yieldably urging the plunger into a groove-engaging position. When in the groove-engaging position, a portion of the plunger extends beyond the outer surface of the body member, with the extending portion adapted to be depressed by a force to move the plunger into a groove-disengaged position. One feature of the foregoing structure is that the plunger is normally biased into the groove-engaging position, and the plunger is depressed to the groove-disengaged position by a force acting substantially perpendicular to the axis of the drill. One advantage of this feature is that the engagement of the grooves by the plunger is unaffected by rotation of the drill bit about the drill bit longitudinal axis. The plunger is disengaged from the appropriate groove only by a force that is applied about the axis substantially perpendicular to the axis of rotation of the drill bit.

Also in preferred embodiments of the present invention, the body member includes a frustaconically-shaped portion that terminates at the first end. One feature of the foregoing structure is that the first end, the depth limiting end, has a smaller diameter than the overall diameter of the body member. One advantage of this feature is that the smaller diameter depth limiting end does not block the surgeon's view of the drill bit and hole as the first end approaches the bone surface to stop the penetration of the drill bit.

The present invention provides a drill assembly that includes an adjustable drill stop that is easily moved and adjusted along the length of the drill bit to control the depth of penetration of the drill bit into a bone. The adjustable stop is operated by a force applied along an axis substantially perpendicular to the axis of the drill bit. Rotation of the drill bit about its axis does not affect in any manner the locking capability of the adjustable stop member. The adjustable drill stop of the present invention is adaptable for use for many types of bone drills, including drills having a reamer and chamfer portion.

Additional objects, features, and advantages of the invention will become apparent to those skilled in the art upon consideration of the following detailed description of a preferred embodiment exemplifying the best mode of carrying out the invention as presently perceived. A detailed description particularly refers to the accompanying figures in which:

BRIEF DESCRIPTION OF THE DRAWINGS

FIG. 1 is a perspective view of the drill assembly of the present invention;

FIG. 2 is an exploded isometric view showing the plunger and spring removed from the body member;

FIG. 3 is a cross sectional view taken along lines 3—3 of FIG. 1;

FIG. 4 is a cross sectional view taken along lines 4—4 of FIG. 3; and

DETAILED DESCRIPTION OF THE DRAWINGS

Figure 5:
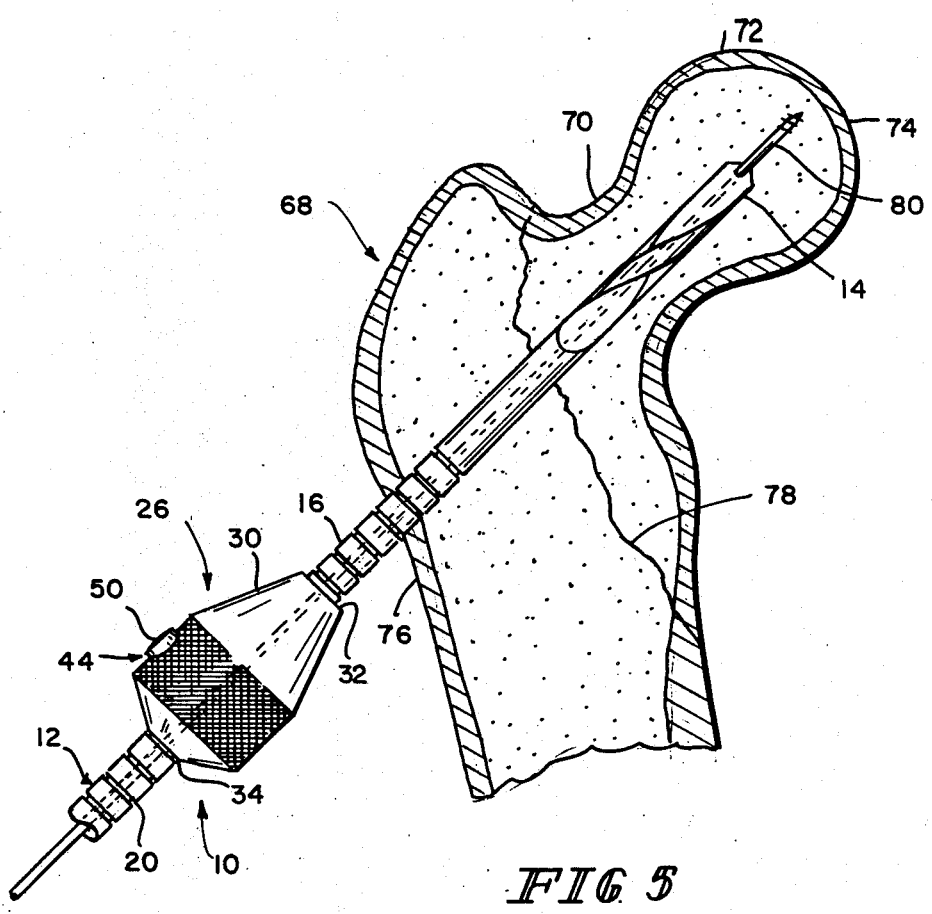
FIG. 5 is a cross sectional view through a fractured femur bone showing the drill assembly in elevation partially extending into the bone.

Referring now to the drawings, and particularly to FIG. 1, FIG. 1 shows the drill assembly 10 of the present invention. The drill assembly 10 includes an elongated drill bit 12 that includes a conventional drilling end 14. The drill bit 12 also includes a shank portion 16 with a plurality of circumferentially extending, axially spaced grooves 20 formed therein. Numerical indicators 22 (FIG. 2) are provided adjacent every other groove 20, the use of which will be discussed later. The drill bit 12 also includes an engaging end 24 that is configured to be received in, and driven by a conventional drill bit driving device (not shown).

An adjustable stop collar 26 is disposed over the shank portion 16 of the drill bit 12. The stop collar 26 is configured to move axially along the shank portion 16, and to be locked at a selected position on the shank portion 16 to limit the depth of penetration of the drill bit 12 into the material to be drilled.

FIG. 2 shows the stop collar 26 in more detail. The stop collar 26 includes a body portion 28. The body portion 28 includes a generally cylindrically-shaped center portion 29 that includes a roughened outer surface that is adapted to aid an operator (not shown) in gripping the stop collar 26. The body portion 28 also includes a frusticonically-shaped section 30 that terminates in a front, depth-limiting end 32. As best seen in FIG. 1, the depth-limiting end 32 is oriented toward the drilling end 14 of the drill bit 12. The body portion 28 also includes an indicating end 34 that is oriented away from the drilling end 14.

A bore 38 is formed to extend axially through the center of the body portion 28. The bore 38 is sized to have a diameter slightly greater than the diameter of the shank portion 16 of the drill bit 12 to permit the shank portion 16 to be movably received within the bore 38. A cavity 40 is formed in the center portion 29 of the body portion 28. The cavity 40 is oriented to be perpendicular to the bore 38, and extends into the body member 28 through the bore 38 to a depth somewhat greater than one-half the diameter of the center portion 29. The orientation and depth of the cavity 40 is best shown in FIGS. 3 and 4.

A generally cylindrically-shaped plunger 44 is provided that is sized and shaped to be movably received into the cavity 40. FIG. 2 shows the plunger 44 removed from the cavity 40 for clarity. The plunger 44 includes an opening 46 that extends transversely therethrough. The opening 46 is oriented to align with the bore 38 when the plunger 44 is placed within the cavity 40. The orientation of the opening 46 and the bore 38 is best shown in FIG. 4. An upstanding ridge 48 is formed on the lower portion of the opening 46. The ridge 48 is sized and shaped to be partially received into any one of the grooves 20 in the shank portion 16. The plunger 44 also includes at one end an upper surface 50 that extends somewhat beyond the outer surface of the center portion 29 of the body portion 28 when the plunger 44 is fitted into the cavity 40 (FIGS. 3 and 4). A reduced diameter portion 52 is formed on the end of the plunger 44 opposite the upper surface 50. The reduced diameter portion 52 and the main portion of the plunger 44 cooperate to define a downwardly facing shoulder 54.

A coil spring 60 is provided to be disposed within the cavity 40 to cooperate with a bottom surface 62 of the cavity 40 to bias the plunger 44 upwardly. The spring 60 is sized to mate with the shoulder 54 on the plunger 44 to provide this biasing force. It will be understood that the spring 60 could be attached to the shoulder 54 of the plunger 44 rather than being separate. FIG. 2 also shows a passage 64 that is formed axially through the drill bit 12. The use of the passage 64 will be described in detail later.

FIG. 3 shows the plunger 44 disposed within the cavity 40 in a position of use with the shank portion 16 of the drill bit 12 extending through the bore 38 and the stop collar 26 and the opening 46 in the plunger 44. The ridge 48 is shown in an engaging position in one of the grooves 20. It will be understood that the plunger 44 is biased to this groove-engaging position by the spring 60. FIG. 3 also shows clearly that the opening 46 is sized somewhat larger than the diameter of the shank portion 16. Specifically, the opening 46 is sized to permit the shank portion 16 to axially move through the opening 46 when the ridge 48 is disengaged from the groove 20.

FIG. 4 shows in greater detail the engagement of the groove 20 by the ridge 48. As discussed previously, the ridge 48 is sized to fit within the groove 20 with very close dimensional tolerance. Because of this close tolerance, when the ridge 48 is engaged with the groove 20, axial movement of the shank portion 16 with respect to the plunger 44 is negligible. As can be seen in FIG. 4, the dimensional tolerance between the plunger 44 and the cavity 40 is also substantially close to prevent movement of the plunger 44 within the cavity 40 transverse to the axis of cavity 40. Thus, when the ridge 48 is engaged with one of the grooves 20 on the shank portion 16, relative axial movement between the stop collar 26 and the drill bit 12 is prevented.

To disengage the ridge 48 from the groove 20, the plunger 44 must be depressed against the biasing force of the spring 60 within the cavity 40. Illustratively, FIG. 4 shows a force applied against the upper surface 50 of the plunger 44 depicted by the arrow 66. In use, the upper surface 50 would normally be depressed by an operator (not shown) in the direction of the arrow 66 to disengage the ridge 48 from the groove 20. Once the plunger 44 has been depressed to disengage the ridge 48 from the groove 20, the shank portion 16 of the drill bit 12 can be axially moved within the stop collar 26 to reposition the drilling end 14 of the bit 12 with respect to the depth limiting end 32 of the stop collar 26.

To determine accurately the length of the drill bit 12 that extends beyond the depth limiting end 32 to the drilling end 14, the markings 22 on the shank portion 16 are used in conjunction with the indicating end 34 of the stop collar 26. The marking 22 immediately adjacent the indicating end 34 serves as an indication of the exposed length of the drill bit 12 between the depth limiting end 32 and the drilling end 14 of the drill bit 12. This exposed length of the drill bit 12 will correspond to the depth of the hole that can be drilled by the drill bit 12 when the stop collar 26 is so oriented.

FIG. 5 shows the drill assembly 10 of the present invention in a position of use in the upper portion of a femur bone 68. Specifically, the drill assembly 10 is shown oriented to drill a hole in the upper portion of the femur 68 from the lateral portion of the femur 68 below the greater trochanter, through the neck 70, and into the head 72 of the femur 68. Illustratively, the hole will be used for the placement of an implant screw (not shown) to stabilize the head 72 and neck 70 with respect to the remaining portion of the femur 68 to reduce a fracture indicated by the fracture line 78.

Before using the drill assembly 10 to drill the pilot hole for the implant screw, a guidewire 80 is first placed within the femur 68 in the same orientation and direction as the desired hole to be drilled. Illustratively, the guidewire 80 is a ⅛ inch diameter guide pin. It will be understood that other types of guide devices could be used. The guidewire 80 is conventionally placed within the femur 68 using a guiding device (not shown) that insures that the guidewire 80 will be properly guided and oriented in the bone 68. The depth of penetration of the guidewire 80 into the head 72 is determined by conventional x-ray techniques. It will be understood that the depth of penetration of the guidewire 80 is critical because of the importance of not penetrating through the outer surface 74 of the head 72. Ideally, the guidewire 80 is placed as deeply as possible into the head 72 without penetrating the outer surface 74. Once the guidewire 80 is in place, a separate instrument (not shown) is used to determine the depth of penetration of the guidewire 80 into the femur 68. It will be understood that the depth of penetration of the guidewire 80 when in place corresponds to the desired depth of the hole to be drilled by the drill assembly 10. Such a corresponding depth will permit the drill assembly 10 to drill a hole extending into the head 72 of the femur 68 without penetrating the outer surface 74.

After the guidewire 80 has been placed within the femur 68, and a depth of penetration of the guidewire 80 ascertained, the stop collar 26 is adjusted over the shank portion 16 until the indicating end 34 is adjacent a marking 22 that corresponds to the depth of penetration of the guidewire 80. The adjustment of the stop collar 26 is conducted by depressing the upper surface 50 of the plunger 44 to disengage the ridge 48 from the groove 20. With the plunger 44 in this position, the shank portion 16 of the drill bit 12 can be axially moved within the stop collar 26 until the indicating end 34 is aligned with the marking 22 corresponding to the desired depth of the hole to be drilled. Once the stop collar 26 is in the correct position, the plunger 44 is released. The biasing force provided by the spring 60 then urges the ridge 48 into the appropriate groove 20 to lock the stop collar with respect to the drill bit 12.

To drill the hole within the femur 68, the axial passage within the drill bit 12 is placed over the guidewire 80, and the drilling end 14 is brought into contact with a lateral bone surface 76 on the femur 68. A conventional driving device (not shown) is attached to the engaging end 24 of the drill bit 12 to rotate the bit 12. It will be understood that the guidewire 80 remains in place to guide the drilling end 14 to insure that the hole formed by the drill bit 12 extends in the appropriate orientation and direction through the neck 70 into the head 72. As the depth limiting end 32 of the stop collar 26 nears the bone surface 76, the frusticonically-shaped section 30 permits the operator to view the bone surface 76 adjacent the hole being formed to accurately determine when contact between the depth limiting end 32 and the bone surface 76 is eminent. Once the depth limiting end 32 contacts the bone surface 76, the operator knows that the hole has been formed to the correct depth. The drill bit 12 is then conventionally removed from the hole, followed by removal of the guidewire 80. The hole is then prepared for receipt of the implant device (not shown) to reduce the fracture.

Applicants' invention provides a drill assembly having an easily adjustable depth limiting device to limit the depth of penetration of a hole in a bone. The depth limiting stop collar 26 is accurately adjustable along the drill bit 12, and is not susceptible to dislodgment due to rotation of the drill bit 12.

Although the invention has been described in detail with reference to a preferred embodiment and specific examples, variations and modifications exist within the scope and spirit of the invention as described and defined in the following claims.

What is claimed is:

1. A drill stop apparatus for use with an elongated drill bit having a drilling end used to drill a hole of a specified, predetermined depth, the drill bit having a plurality of circumferentially extending, axially spaced grooves formed thereon, the stop comprising,
    a body member having a first end and formed to include an axially extending bore sized to receive said drill bit to permit said drill bit to be moved axially within said body member,
    said body member also formed to include a cavity that extends substantially perpendicular through said bore, and
    a plunger disposed in said cavity for releasably engaging one of said plurality of grooves in said drill bit to lock said drill bit against axial movement within said body member such that a specified length of said drill bit extends beyond said first end of said body member to define a specified operable drilling length of said drill bit between said first end and said drilling end, said plunger formed to include a transverse opening therethrough sized to receive said drill bit, said transverse opening including a ridge formed therein configured to engage selectively any one of said grooves in said drill bit to lock said drill bit against axial movement within said body member when said plunger is in a groove-engaging position, wherein a portion of said plunger extends beyond the outer surface of said body member, said extending portion adapted to be depressed by a force applied along an axis substantially perpendicular to the axis defined by said body member bore to move said plunger into a groove-disengaged position and spring means for yieldably urging said plunger into said groove-engaging position.

2. The apparatus of claim 1, wherein said body member includes a frustoconically-shaped portion that terminates at said first end.

3. A drill assembly for forming a hole of a specified depth in a bone for receiving a fracture-reducing implant, the assembly comprising,
    a drill bit having an elongated shaft and a drilling end, the shaft including a plurality of circumferentially extending, axially spaced grooves formed thereon,
    a stop member formed to include an axially extending bore sized to receive said shaft of said drill bit to permit said stop member to be moved axially along said shaft, and
    a plunger configured to releasably engage one of said shaft grooves at a selected location along said shaft, the plunger being movable in said stop member along a plane substantially perpendicular to said shaft to releasably lock said stop member against movement along said shaft to define an operable portion of the drill bit between the stop member and the drilling end of the drill bit, the plunger being movable in response to a force applied along an axis that is substantially perpendicular to an axis defined by the stop member bore.

4. The assembly of claim 3, wherein said stop member is formed to include a cavity that extends substantially perpendicular to said stop member bore, and wherein said plunger is formed to include a hole extending therethrough and a ridge disposed in said hole, said plunger being sized to be received within said cavity such that said drill shaft extends through said hole and said ridge is sized and configured to selectively engage one of said shaft grooves to lock said stop member against movement with respect to said drill shaft.

5. The assembly of claim 4, wherein said plunger is movable between a groove-engaging position and a groove-disengaged position, and further comprising a spring to yieldably bias said plunger to the groove-engaging position.

6. The assembly of claim 5, further comprising a spring to yieldably bias said plunger to said groove-engaging position.

7. The assembly of claim 5, wherein said plunger operates along an axis that is generally perpendicular to the longitudinal axis of said drill bit.

8. A drill bit stop apparatus for use with a drill bit having an elongated shaft defining a first axis and having a cutting end and a plurality of circumferentially extending, axially spaced grooves formed thereon, the apparatus comprising,
    a body member having a first end and configured to be slidably received for movement over said elongated shaft along said first axis, and
    finger operated plunger means disposed within said body member for releasably engaging one of said plurality of said shaft grooves to lock said body member against movement along said first axis on said shaft while permitting rotational movement of the body member with respect to the shaft, said plunger means movable in response to a force applied along an axis substantially perpendicular to the first axis between a groove-engaging position and a groove-disengaging position, and
    spring means for yieldably urging said plunger into the groove-engaging position.

9. The apparatus of claim 8, wherein said plunger means comprises a plunger member formed to include a passageway substantially aligned with said first axis and configured to receive said drill bit shaft and an upstanding ridge formed in said passageway, said ridge adapted to engage one of said plurality of shaft grooves when said plunger member is in a groove-engaging position.

10. An adjustable drill stop for use with an elongated drill having circumferentially extending, axially spaced grooves formed thereon, the stop comrprising, a generally cylindrical housing formed to include a bore extending axially entirely through said housing, said housing also formed to include a cavity that extends into said housing through said aperture, said cavity oriented substantially perpendicular to said aperture, a finger-operated plunger disposed in said cavity, said plunger formed to include an opening that is sized and oriented to receive a portion of said drill bit and including a ridge formed in said opening that is configured to releasably engage one of said grooves formed on said drill bit, said plunger movable from a groove-engaged position to a groove-disengaged position by application of a plunger-depressing force applied along an axis substantially perpendicular to an axis defined by said bore, and a spring for releasably biasing said plunger to the groove-engaging position.

* * * * *

UNITED STATES PATENT AND TRADEMARK OFFICE
CERTIFICATE OF CORRECTION

PATENT NO. : 4,710,075

DATED : December 1, 1987

INVENTOR(S) : Dale Davison

It is certified that error appears in the above-identified patent and that said Letters Patent is hereby corrected as shown below:

At column 3, line 43, please delete "frustaconically-" and insert therefor --frustoconically---;

At column 4, line 43, please delete "frusticonically-shaped" and insert therefor --frustoconically-shaped--;

At column 7, line 3, please delete "frusticonically-shaped" and insert therefor --frustoconically-shaped--;

At column 7, line 14, please delete "Applicants'" and insert therefor --Applicant's--;

At column 7, line 19, please delete "suspectible" and insert therefor --susceptible--; and At column 9, line 2, after the word "drill" insert the word --bit--.

Signed and Sealed this

Twenty-fourth Day of May, 1988

Attest:

DONALD J. QUIGG

*Attesting Officer*   *Commissioner of Patents and Trademarks*